(12) United States Patent
Baxter et al.

(10) Patent No.: US 10,433,991 B2
(45) Date of Patent: Oct. 8, 2019

(54) CONTROLLED EXPANSION STENT GRAFT DELIVERY SYSTEM

(71) Applicant: Cook Medical Technologies LLC, Bloomington, IN (US)

(72) Inventors: Charles Baxter, West Lafayette, IN (US); Ryan Bradway, Tacoma, WA (US); Jarin Kratzberg, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 242 days.

(21) Appl. No.: 15/582,846

(22) Filed: May 1, 2017

(65) Prior Publication Data

US 2018/0014955 A1 Jan. 18, 2018

Related U.S. Application Data

(60) Provisional application No. 62/363,604, filed on Jul. 18, 2016.

(51) Int. Cl.
*A61F 2/95* (2013.01)
*A61F 2/962* (2013.01)
*A61F 2/966* (2013.01)
*A61F 2/07* (2013.01)

(52) U.S. Cl.
CPC ............... *A61F 2/95* (2013.01); *A61F 2/07* (2013.01); *A61F 2/966* (2013.01); *A61F 2/962* (2013.01); *A61F 2002/9511* (2013.01); *A61F 2002/9517* (2013.01); *A61F 2002/9665* (2013.01); *A61F 2220/0033* (2013.01); *A61F 2250/001* (2013.01)

(58) Field of Classification Search
CPC .................... A61F 2/95–97; A61F 2/07; A61F 2002/9505–9665; A61F 2002/072–077; A61F 2/01–013; A61F 2002/011–018
See application file for complete search history.

(56) References Cited

U.S. PATENT DOCUMENTS

| 4,889,137 | A | * | 12/1989 | Kolobow ................ A61F 2/88 128/898 |
| 5,665,115 | A | | 9/1997 | Cragg |
| 6,117,140 | A | * | 9/2000 | Munsinger ............. A61F 2/95 606/108 |
| 6,221,096 | B1 | | 4/2001 | Aiba et al. |

(Continued)

FOREIGN PATENT DOCUMENTS

| EP | 2298248 | 3/2011 |
| EP | 2471498 | 7/2012 |

OTHER PUBLICATIONS

European Patent Office, European Search Report for Application No. 17181300.9, Published Nov. 7, 2017, Munich Germany.

*Primary Examiner* — Jonathan A Hollm
(74) *Attorney, Agent, or Firm* — Liell & McNeil

(57) ABSTRACT

A controlled expansion stent graft delivery system has an adjustment configuration in which a retractable sheath is at a retracted position out of contact with a stent graft, but expansion of the stent graft is controlled by a control tether, which has a middle segment wrapped around a fabric tube of the stent graft. The stent graft changes diameter responsive to a tension level in the control tether. At least one of an orientation and a position of the stent graft may be adjusted during controlled expansion via the control tether.

20 Claims, 4 Drawing Sheets

(56) References Cited

U.S. PATENT DOCUMENTS

| | | | |
|---|---|---|---|
| 6,280,465 B1 * | 8/2001 | Cryer | A61F 2/95 |
| | | | 623/1.11 |
| 6,346,118 B1 | 2/2002 | Baker et al. | |
| 8,043,354 B2 | 10/2011 | Greenberg et al. | |
| 8,114,145 B2 | 2/2012 | Hartley et al. | |
| 8,262,718 B2 | 9/2012 | Chuter et al. | |
| 8,414,633 B2 * | 4/2013 | Sisken | A61F 2/958 |
| | | | 623/1.11 |
| 8,551,158 B2 | 10/2013 | Roeder et al. | |
| 8,709,059 B1 | 4/2014 | Shriver | |
| 8,715,337 B2 | 5/2014 | Chuter | |
| 8,740,969 B2 | 6/2014 | Jensen et al. | |
| 2003/0050684 A1 | 3/2003 | Abrams et al. | |
| 2004/0098079 A1 | 5/2004 | Hartley et al. | |
| 2008/0294234 A1 | 11/2008 | Hartley et al. | |
| 2012/0046652 A1 | 2/2012 | Sokel | |
| 2012/0101563 A1 | 4/2012 | Zhu et al. | |
| 2012/0172965 A1 * | 7/2012 | Kratzberg | A61F 2/962 |
| | | | 623/1.12 |
| 2013/0046373 A1 | 2/2013 | Cartledge et al. | |

* cited by examiner

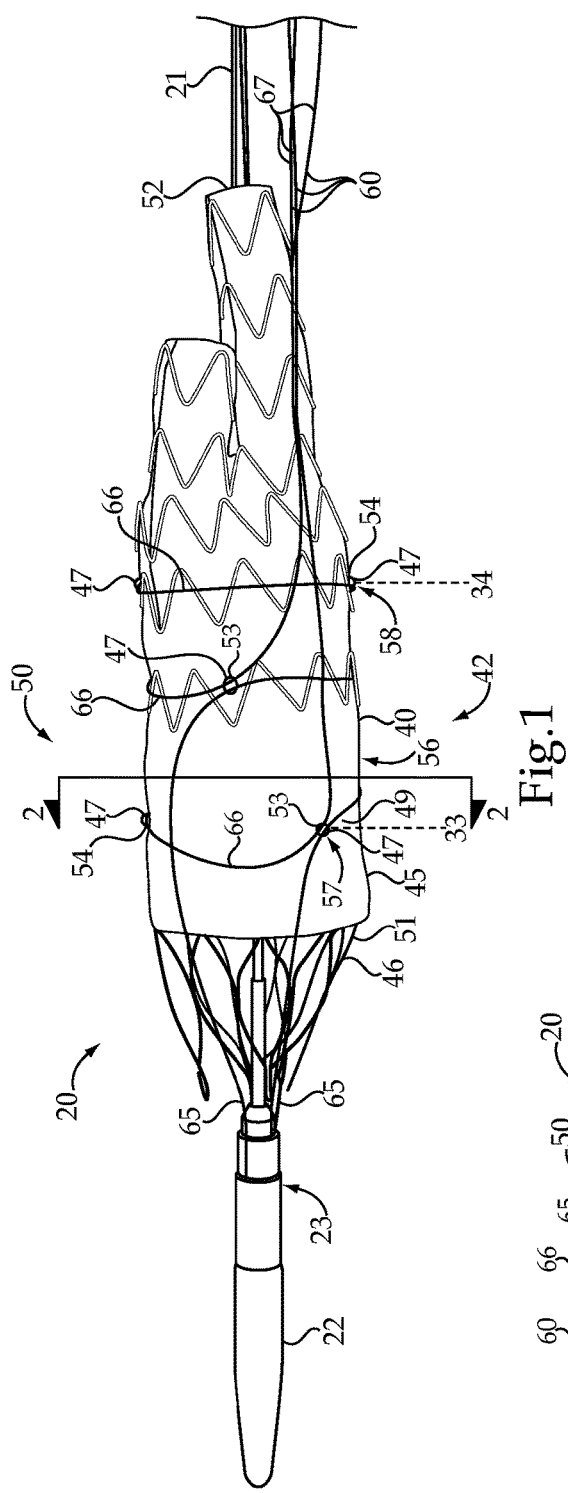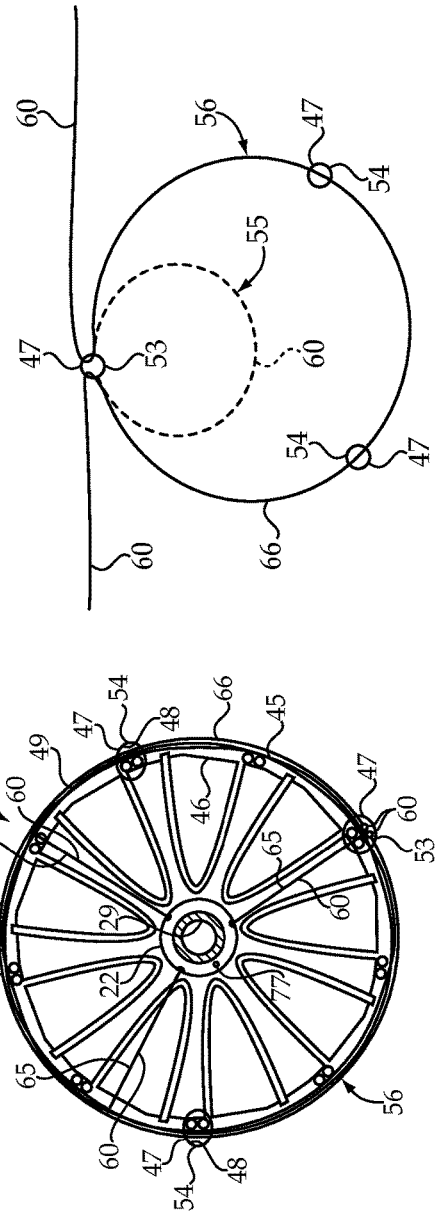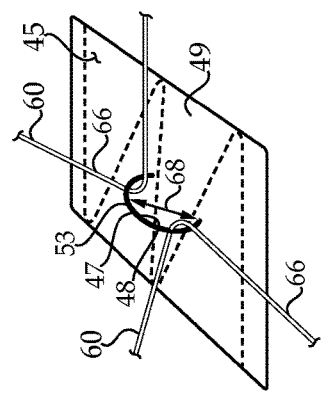

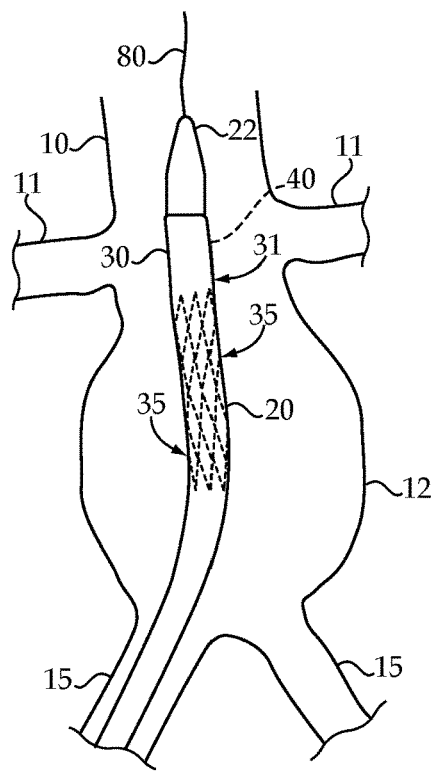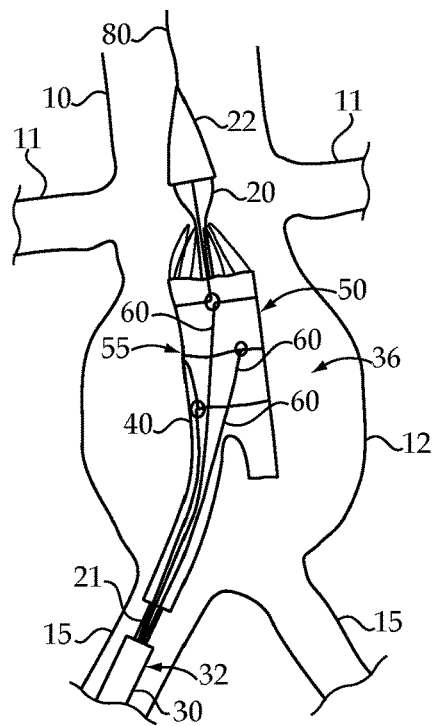
Fig.10    Fig.11
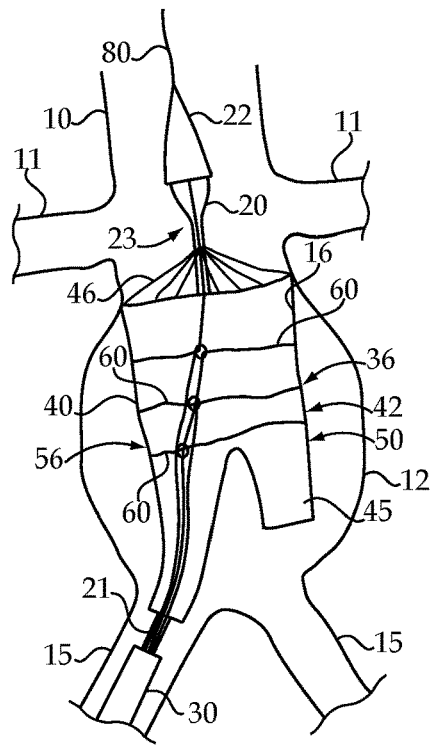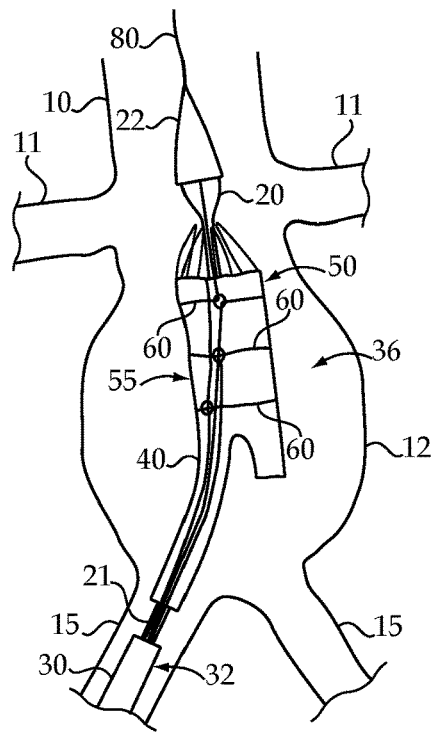
Fig.12    Fig.13

CONTROLLED EXPANSION STENT GRAFT DELIVERY SYSTEM

TECHNICAL FIELD

The present disclosure relates generally to stent graft delivery systems, and more particularly to controlled expansion of stent grafts that may have orientation and/or positioning sensitivities.

BACKGROUND

Some variability is involved with placing stent grafts when un-sheathing and allowing full expansion utilizing known self-expanding stent designs. Some stent grafts, such as those located in the aorta, require precise placement and are often delivered by unsheathing the device to a secondary constrained diameter. From this point, the clinician may interpolate the stent graft's likely landing zone, and release the stent graft to self-expand to its final diameter opposed to a vessel wall. This process can introduce variability in a final landing zone due to the jump that occurs between the intermediate and final diameters in which the device is not constrained to the delivery system. During this brief period of time, blood flow and other factors can impact the trajectory of the stent graft changing its final landing zone. Problems can occur when the final landing zone is different from the intended landing zone for the stent graft, either in position or orientation, or both.

The present disclosure is directed toward one or more of the problems set forth above.

SUMMARY

In one aspect, a stent graft and control tether assembly includes a fabric tube attached to, and supported by, a self expanding stent. A plurality of loops are attached to at least one of the fabric tube and the self expanding stent, and each of the loops has an opening exposed on a radially outward side of the fabric tube. A control tether has a first segment, a middle segment, and a second segment. The middle segment is wrapped around the fabric tube and received through the opening of each of the loops. The first segment extends beyond one end of the fabric tube, while the second segment, which is longer than the first segment, extends beyond an opposite end of the fabric tube.

In another aspect, a controlled expansion stent graft delivery system includes a retractable sheath and a delivery catheter with a tip that includes a tether clamp. A stent graft includes a plurality of loops attached to at least one of a fabric tube and a self expanding stent, and each of the loops has an opening exposed on a radially outward side of the fabric tube. The delivery system has a delivery configuration in which the stent graft is mounted on the delivery catheter in a compressed state and covered by the retractable sheath. The delivery system is movable from the delivery configuration to an adjustment configuration in which the retractable sheath is at a retracted position out of contact with the stent graft, and a control tether is held by the tether clamp, wrapped around the stent graft, and received through the openings of the loops. The delivery system is movable from the adjustment configuration to a release configuration in which the control tether is released from the tether clamp, wrapped around the stent graft, and received through the openings of the loops. The delivery system is movable from the release configuration to a detached configuration in which the stent graft is in an expanded state, and the control tether is out of contact with the stent graft.

BRIEF DESCRIPTION OF THE DRAWINGS

FIG. 1 is an enlarged side view of a stent graft and control tether assembly mounted on the delivery system, which is partially shown;

FIG. 2 is a sectioned view through the assembly of FIG. 1 as viewed along section lines 2-2;

FIG. 3 is a schematic view of the control tether being tensioned between reduced and enlarged diameter configurations;

FIG. 4 is a close up perspective view through one of the loops of FIG. 1;

FIG. 10 is a schematic view of a controlled expansion stent graft delivery system being maneuvered through an aorta in a delivery configuration;

FIG. 11 shows the delivery system moved from the delivery configuration of FIG. 10 to an adjustment configuration;

FIG. 12 is a schematic view of the delivery system in the adjustment configuration with the stent graft expanded;

FIG. 13 is a schematic view of the delivery system an adjustment configuration with the stent graft partially expanded;

DETAILED DESCRIPTION

Figure 5:
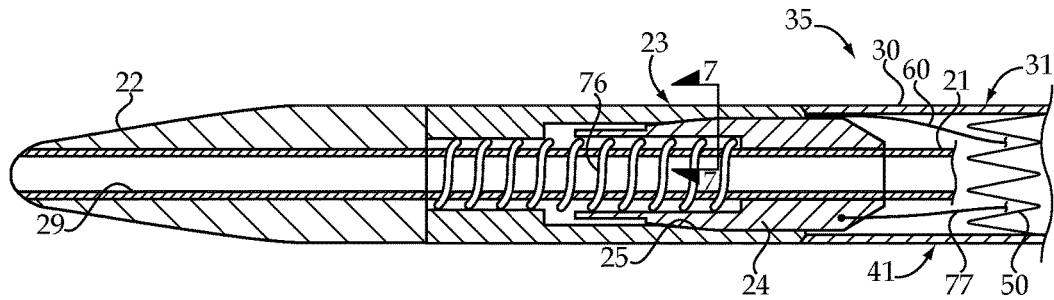
FIG. 5 is an enlarged schematic sectioned view of the tip of a delivery catheter for the delivery system of FIG. 1.
Figure 6:
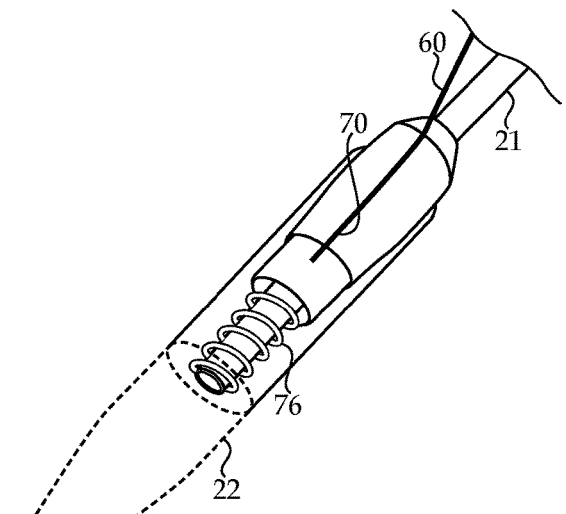
FIG. 6 is an enlarged see-through perspective view of the tip region of the delivery system of FIG. 1.

Referring initially to FIGS. 1-9, a controlled expansion stent graft delivery system 20 is utilized to deliver a stent graft 40 to a treatment location in a patient. In the illustrated embodiment, stent graft 40 includes a fabric tube 45 that is attached to, and supported by, a self expanding stent 46, and is shaped for treatment of an abdominal aortic aneurysm in a manner known in the art. Stent graft 40 is a portion of an assembly 50 so that includes at least one control tether 60. Apart from a stent graft and control tether assembly 50, the delivery system 20 includes a delivery catheter 21 with a tip 22 that includes a tether clamp 23. A retractable sheath 30 is slidably movable with regard to the delivery catheter 21 in a manner well known in the art. In addition to the sutures that may or may not be included to attach the fabric tube 45 to the self expanding stent 46, the stent graft 40 includes a plurality of loops 47 that are attached to at least one of the fabric tube 45 and the self expanding stent 46. Loops 47 may be formed with suture material. Each of the loops 47 has an opening 48 exposed on a radially outward side 49 of fabric tube 45. Each of three control tethers 60 in the illustrated embodiment includes a first segment 65, a middle segment 66 and a second segment 67. Each middle segment 66 is wrapped around the fabric tube 45 and is received through the opening 48 of the loops 47 at each of three different longitudinal positions along stent graft 40. The first segment 65 of each of the control tethers 60 extends beyond one end 51 of the fabric tube 45. Each of the second segments 67, which are longer than the respective first segments 65, extends beyond an opposite end 52 of the fabric tube 45.

As partially shown in FIG. 5, delivery system 20 has a delivery configuration 35 in which the stent graft 40 is mounted on the delivery catheter 21 in a compressed state 41 and covered by the retractable sheath 30, which is at a covering position 31. The delivery system 20 is movable from the delivery configuration 35 shown in FIG. 5 to an adjustment configuration 36 (FIGS. 11-13) in which tension in the control tethers 60 keep the stent graft 40 from fully expanding to allow the user to adjust a position and/or an orientation of the stent graft 40 in-vitro. The delivery system 20 may be moved from the adjustment configuration 36 to a release configuration 37 (FIG. 8) with the stent graft in an expanded state 42 after the positioning and orientation of the stent graft 40 have been adjusted by the user to a desired landing zone in the treatment vessel. Thereafter, the delivery system 20 may be movable from the release configuration 37 to a detached configuration 30 in which the stent graft 40 is in the expanded state 42 and the control tether(s) 60 is out of contact with the stent graft 40. Thus, the use of the control tether(s) 60 allows the user to controllably expand, shrink and re-expand the stent graft 40 in-vitro to better position the stent graft 40 at a desired position and orientation within a patient.

In the example embodiment shown in FIGS. 1 and 2, stent graft 40 includes a first set 57 of three loops 47 located at a first longitudinal location 33, and a second set 58 of at least three loops 47 at a second longitudinal location 34 that is spaced along the longitudinal axis from the first set of loops 57. In addition, a third set of at least three loops 47 is located at a longitudinal position between the first longitudinal location 33 and the second longitudinal location 34. Although each longitudinal location has three loops, one, two or four or more loops at each location would also fall within the scope of this disclosure. These spaced apart longitudinal positions are chosen such that when the tension is applied to the control tethers 60, the respective middle segments 66 can be used to change the self expanding stent 46 between a reduced diameter configuration 55 (FIG. 3) when the control tether(s) 60 is in tension, and an enlarged diameter configuration 56 (FIGS. 1-3) when the control tether(s) 60 has reduced or no tension. As best shown in FIG. 4, the opening 48 defined by each of the loops 47 is at least several times larger than the diameter 68 of the respective control tether 60 so that the control tether 60 is freely slidable through the respective opening 48. In the illustrated embodiment, the loops 47 have been shown added to a conventional AAA bifurcated main body graft of the type manufactured by Cook Inc., but the present disclosure is also applicable to stent grafts for virtually any treatment application, especially those requiring precise placement and orientation. Each of the respective control tethers 60 is received through one of the loops 53 in the respective set of loops 57 or 58 exactly twice and received through the other loops 54 of that respective set of loops exactly once. This feature is shown for example in FIG. 2, and partially shown in FIGS. 1, 3 and 4.

When delivery system 20 is in either the delivery configuration 35 (FIG. 10) and an adjustment configuration 36 (FIGS. 11-13) to be described infra, the first segment 65 of each of the respective control tethers 60 is held by the tether clamp 23, which forms a portion of tip 22. Thus, by jailing first segments 65, a user can apply tension to the remote end of second segment 67 to control shrinkage and expansion of the stent graft 40 between the reduced diameter configuration 55 and the enlarged diameter configuration 56. The stent graft 40 changes its diameter responsive to a tension level in the control tether(s) 60 when the delivery system 20 is in its adjustment configuration 36. In fact, the user may actually reduce the diameter of stent graft 40 responsive to an increase in the tension level of the control tether(s) 60 when the delivery system 20 is in the adjustment configuration 36. The tension level in the control tether 60 acts in opposition to the spring tendency of the self expanding stent 46 to expand.

Figure 7:
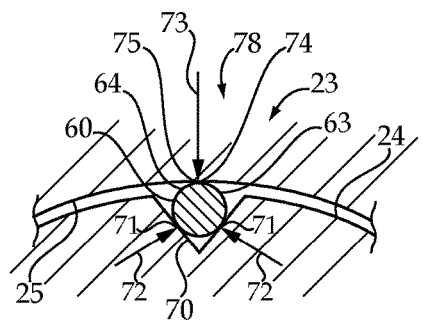
FIG. 7 is a partial sectioned view through the tether clamp of FIG. 5 in a clamped position.
Figure 8:
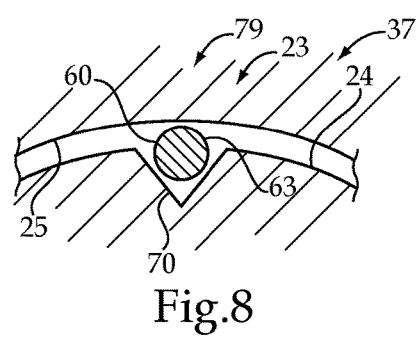
FIG. 8 is a partial sectioned view of through the tether clamp in a release position.
Figure 9:
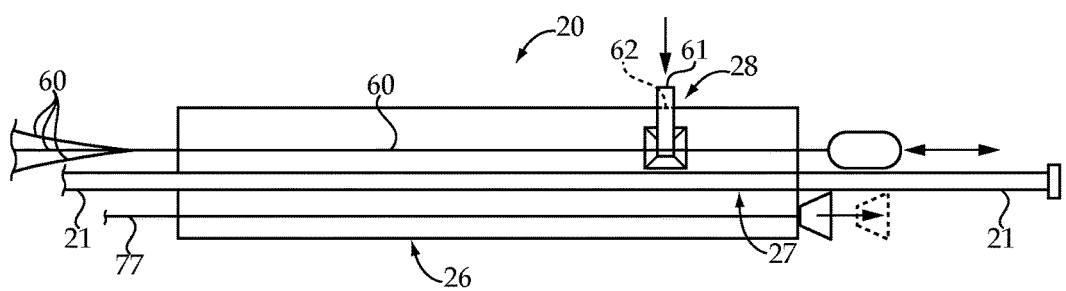
FIG. 9 is a schematic view of a handle for the delivery system of FIG. 1.

Although tether clamp 23 can take on a wide variety of different forms, in the illustrated embodiment as best shown in FIGS. 5-8, the illustrated tether clamp 23 includes a male part 24 that is mated to a female part 25. In the illustrated embodiment, tether clamp 23 includes a tension spring 76 that is operably positioned to bias the male part 24 and the female part 25 toward a clamped position 78 as shown in FIG. 7. A clamp release line 77 may be connected to tether clamp 23 in general, and in the illustrated embodiment to the male part 24 in particular. The tether clamp 23 can move from the clamped position as shown in FIG. 7 toward a release position 79 as shown in FIG. 8 responsive to tension in the clamp release line 77 overcoming the bias of spring 76. Thus, after the stent graft 40 is precisely placed, the tether clamp 23 can be moved to its release position 79 to allow the control tether(s) 60 to be withdrawn toward a handle 26 of delivery system 20 and out of contact with stent graft 40. FIG. 9 shows a schematic view of handle 26 that is attached to delivery catheter 21 at an end 27 opposite to that of tip 22. One or more cleats 28 may be attached to handle 26. The control tether(s) 60 has a first position 61 cleated to the cleat 28, and a second position 62 released from cleat 28. In the illustrated embodiment, the three control tethers 60 are shown as merged into a single control tether 60 before contacting cleat 28 so that the three control tethers 60 shown in FIG. 1 can be simultaneously tensioned and un-tensioned responsive to movement of the remote end of the control tether 60 relative to cleat 28 as shown in FIG. 9. The cleat 28 allows a user to retain a desired amount of tension in the control tether(s) 60 by moving cleat 28 to its cleated position. On the otherhand, the user may increase or decrease tension in the control tether(s) 60 and allow the self expanding stent 46 to pull the control tether 60 toward stent graft 40, or in a reverse direction to increase tension against the action of the self expanding stent 46. As used in the present disclosure, a "cleat" means any structure that allows the control tether(s) 60 to be held in tension, hands free, but is releasable to allow the tension in the control tether(s) 60 to be changed. Thus, according to the present disclosure, a cleat may or may not include movable parts and maybe anything from a simple valley shaped wedge that may grip the tether 60 to a movable spring loaded clamp like structure without departing from the present disclosure.

Although not necessary, each control tether 60 may be a monofilament wire 63, with the tether clamp 23 constructed to contact the monofilament wire 63 at three spaced apart locations 73 around a circumference 64 of the monofilament wire 63 as best shown in FIG. 7. In order to have the three point clamping configuration as shown in FIG. 7, one of the male part 24 and the female part 23 defines a v-shaped groove 70 that includes two of three clamping surfaces 71 that contact the monofilament wire 63 at two of three spaced apart locations 73. The other one of the male part 24 and female part 25 includes a clamping surface 74 that contacts the monofilament wire 63 at a remaining one 75 of the three spaced apart locations 73. Those skilled in the art will appreciate that other clamping configurations could be utilized, and the control tether(s) could be multifilament instead of the monofilament wire 63 of the illustrated embodiment.

Figure 15:
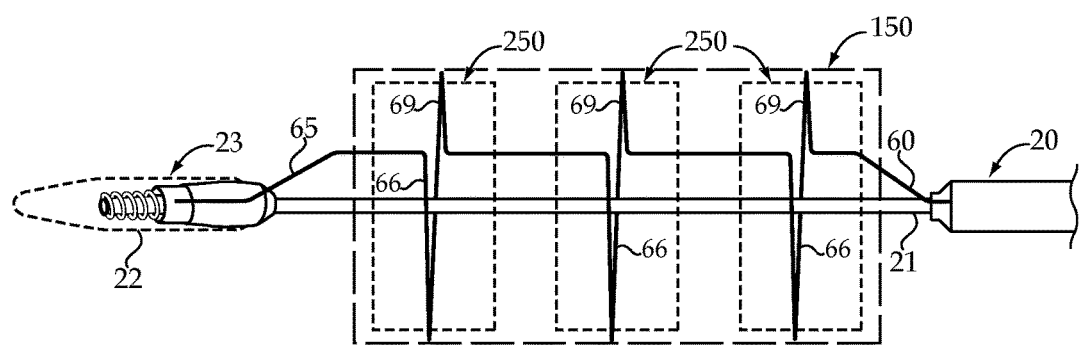
FIG. 15 is a schematic view of two more variations of a stent graft delivery system according to the present disclosure.

Referring now in addition to FIG. 15, a couple of different variations of a stent graft and control tether assembly 150 and 250 are shown. With regard to assembly 150, a single stent graft is schematically shown and has a single control tether 60 wrapped around the stent graft so that middle segment 66 wraps around the fabric tube a first time and a second time 69 and the third time, thus illustrating that each control tether may wrap around an individual stent graft more than one time at different longitudinal locations along the stent graft. Also shown, is an assembly 250 in which three separate stent grafts share a common single control tether 60 such that each of the three stent grafts has a middle segment 66 of the control tether 60 wrapped one time around each of the three stent grafts. Thus, those skilled in the art will appreciate that the present disclosure is applicable to delivery assemblies for delivering more than one stent graft that share a common control tether and to a single stent graft that uses only one control tether wrapped around the stent graft more than one time. This is to be contrasted with the illustrated embodiment in which three control tethers 60 are used with each of the control tethers 60 being wrapped around the stent graft 40 one time. Those skilled in the art will appreciate that other permutations would also fall within the scope of this disclosure.

INDUSTRIAL APPLICABILITY

The present disclosure finds general applicability to any self expanding stent graft. The present disclosure finds particular applicability to stent grafts with sensitivities to placement location and/or orientation, such as for accommodating branch vessels. The present disclosure finds specific applicability for delivering stent grafts to high flow areas, such as those associated with the aorta, which also include many branching arteries that must be accommodated by proper placement and orientation of a stent graft.

Referring now in addition to FIGS. 10-14, an example method of operating a controlled expansion stent graft delivery system 20 is shown for treating an aneurysm 12 in the aorta 10 that is located immediately below branching vessels, which may include the renal artery 11. The delivery system 20 may approach the implantation site utilizing a previously placed wire guide 80 utilizing an access in the patient's leg (not shown) and travel up through the iliac artery 15. Wire guide 80 may be received through a lumen 29 of delivery catheter 21. In particular, the delivery system 20 is positioned at a treatment site in a delivery configuration 35 in which the stent graft 40 is mounted on delivery catheter 21 in a compressed state 41 and covered by retractable sheath 30, which is at a covering position 31. Next, as shown in FIG. 11, the delivery system is moved to the adjustment configuration 36 with the retractable sheath 30 moved from the covering position 31 shown in FIG. 10 to the retracted position 32 to uncover the stent graft 40. When in the adjustment configuration 36, the control tethers 60 have sufficient tension to prevent the stent graft 40 from fully expanding. When in this configuration, the retractable sheath 30 is out of contact with the stent graft 40. However, the control tethers 60 are held by the tether clamp 23, are wrapped around the stent graft 40, and received through the openings 48 in the individual loops 47 of the stent graft 40.

Figure 14:
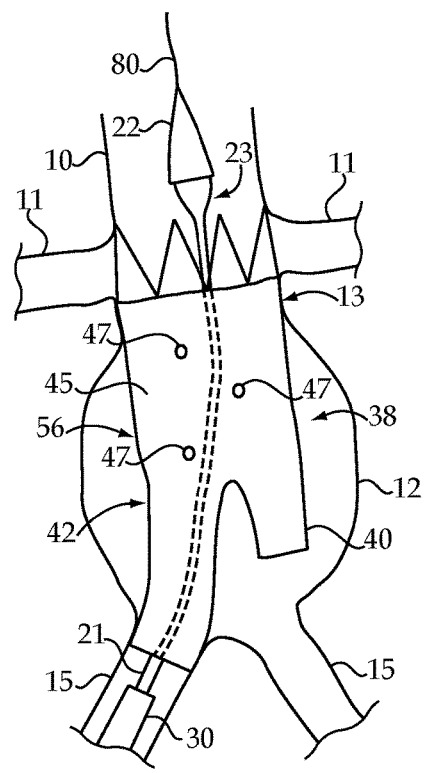
FIG. 14 is a schematic view of the delivery system of FIG. 10 in a detached configuration.

The delivery system 20 is changed from the delivery configuration of FIG. 10 to the adjustment configuration 36, thus allowing the user to make some orientation change via rotating delivery system 20 about its longitudinal axis and positioning adjustments by advancing or retracting the delivery system 20 with regard to the aneurysm 12. When the user believes that the stent graft 40 is properly positioned, tension on the control tethers 60 may be relaxed by uncleating the remote end of control tether 60 from cleat 28 and allow the self expanding stent 46 to move the stent graft 40 into contact with the vessel wall at an initial landing zone 16. The user can then use known visualization strategies to assess both the orientation and placement of stent graft 40 while the delivery system 20 is still in an adjustment configuration 36. The difference between the adjustment configuration 36 shown in FIG. 11 and that shown in FIG. 12 is associated with the level of tension in the control tether(s) 60. If the physician deems that the initial landing zone 16 is not acceptable, the tension level in the control tethers 60 may be increased to shrink the diameter of stent graft 40 as shown in FIG. 13. When in the adjustment configuration 36, the user may adjust the orientation and position of the stent graft 40, and then relieve tension on the control tether(s) 60 so that the stent graft 40 is controllably expanded to the desired landing zone 13 as shown in FIG. 14. After confirming the proper placement of stent graft 40, the physician may release the top stent proximal fixation that are adjacent the renal artery 11 in a manner well known in the art. Next, after confirming a proper seal, the delivery system 20 may be moved from the adjustment configuration 36 to a release configuration 37 (FIG. 8) in which the control tether is released from the tether clamp 23, but remains wrapped around the stent graft 40 and received through the openings 48 of the loops 47, and the stent graft 40 is in its expanded state 42. This is accomplished by pulling the clamp release line 77 to move the clamp 23 from the clamp position shown in FIG. 7 to the unclamped positioned shown in FIG. 8. Thereafter, the delivery system 20 may then be moved from the release configuration 37 to a detached configuration 38 as shown in FIG. 14 in which the stent graft 40 is at the expanded state 42 and the control tether 60 is slid out of contact with the stent graft 40. This is accomplished because the first segment 65 of the individual control tether(s) have been released from tether clamp 23, and withdrawn back through loops 47 toward handle 26 and out of contact with the stent graft 45. Next, the user may withdraw the delivery system 20 leaving the stent graft 40 implanted in a desired position and orientation.

Those skilled in the art will appreciate that while the delivery system 20 is in the adjustment configuration 36 as shown in FIGS. 11-13, the expansion of stent graft 40 may be stopped by increasing tension in the control tether(s) 60. The user may then adjust at least one of the orientation and position of the stent graft 40 while expansion of the stent graft 40 has been stopped. Thereafter, the expansion of the stent graft may be controllably resumed by decreasing tension in control tether 60. The expansion of the stent graft 40 may be stopped by securing the control tether 60 in a cleat 28, which may be attached to handle 26. If the positioning and/or orientation are not as desired, the stent graft 40 may be contracted toward the compressed state 41 by increasing tension in the control tether 60 while the delivery system 20 is in the adjustment configuration 36. As discussed earlier, after proper placement, the tether clamp 23 may be moved from its clamped position 78 to its release position 79 responsive to increasing tension in the clamped release line 77.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A stent graft and control tether assembly comprising:
a fabric tube attached to, and supported by, a self expanding stent that defines a longitudinal axis;
a plurality of loops attached to at least one of the fabric tube and the self expanding stent, and each of the loops having an opening exposed on a radially outward side of the fabric tube;
a control tether with a first segment, a middle segment and a second segment;
the middle segment being wrapped substantially completely around the longitudinal axis at the radially outward side of the fabric tube and being received through the opening of each of the loops;
the first segment extending beyond one end of the fabric tube;
the second segment, which is longer than the first segment, extending beyond an opposite end of the fabric tube.

2. The stent graft and control tether assembly of claim 1 wherein the opening of each of the loops is at least several times larger than a diameter of the control tether so that the control tether is freely slidable through the respective opening.

3. The stent graft and control tether assembly of claim 2 wherein the control tether is received through one of the loops exactly twice and received through an other one of the loops exactly once.

4. The stent graft and control tether assembly of claim 1 wherein the self expanding stent has a reduced diameter configuration when the control tether is in tension; and
the self expanding stent has an enlarged diameter configuration when the control tether is untensioned.

5. The stent graft and control tether assembly of claim 1 wherein the plurality of loops is a first set of at least three loops located at a first longitudinal location;
a second set of at least three loops at a second longitudinal location spaced longitudinally from the first set of loops; and
the middle segment being wrapped around the fabric tube a second time and being received through the opening of each of the loops of the second set of at least three loops.

6. The stent graft and control tether assembly of claim 5 wherein the opening of each of the loops is at least several times larger than a diameter of the control tether so that the control tether is freely slidable through the respective opening;
the control tether is received through one loop in each of first and second sets of loops exactly twice and received through a remaining loops in each of the first and second sets of loops exactly once; and
wherein the self expanding stent has a reduced diameter configuration when the control tether is in tension, and the self expanding stent has an enlarged diameter configuration when the control tether is untensioned.

7. A controlled expansion stent graft delivery system comprising:
a delivery catheter with a tip that includes a tether clamp;
a retractable sheath;
a stent graft that includes a fabric tube attached to, and supported by, a self expanding stent that defines a longitudinal axis, and a plurality of loops attached to at least one of the fabric tube and the self expanding stent, and each of the loops having an opening exposed on a radially outward side of the fabric tube;
a control tether;
the delivery system having a delivery configuration in which the stent graft is mounted on the delivery catheter in a compressed state and covered by the retractable sheath;
the delivery system being moveable from the delivery configuration to an adjustment configuration in which the retractable sheath is at a retracted position out of contact with the stent graft, and the control tether is held by the tether clamp, wrapped substantially completely around the longitudinal axis at the radially outward side of the fabric tube, and received through the openings of the loops;
the delivery system being moveable from the adjustment configuration to a release configuration in which the control tether is released from the tether clamp, wrapped around the stent graft, and received through the openings of the loops, and the stent graft is in an expanded state; and
the delivery system being moveable from the release configuration to a detached configuration in which the stent graft is in the expanded state and the control tether is out of contact with the stent graft.

8. The delivery system of claim 7 wherein the stent graft changes a diameter responsive to a tension level in the control tether when the delivery system is in the adjustment configuration.

9. The delivery system of claim 8 wherein the stent graft reduces the diameter responsive to an increase in the tension level in the control tether when the delivery system is in the adjustment configuration.

10. The delivery system of claim 7 wherein the tether clamp includes a male part mated to a female part.

11. The delivery system of claim 10 wherein the tether clamp includes a spring operably positioned to bias the male part and the female part toward a clamped position;
a clamp release line connected to the tether clamp; and
wherein the tether clamp moves from the clamped position toward a release position responsive to tension in the clamp release line overcoming the bias of the spring.

12. The delivery system of claim 7 wherein the control tether is received through one of the loops exactly twice and received through an other one of the loops exactly once.

13. The delivery system of claim 7 including a handle attached to the delivery catheter at an end opposite to the tip;
a cleat attached to the handle, and the control tether having a first position cleated to the cleat, and a second position released from the cleat.

14. The delivery system of claim 7 wherein the control tether is a monofilament wire; and
the tether clamp contacts the monofilament wire at three spaced apart locations around a circumference of the monofilament wire.

15. A controlled expansion stent graft delivery system comprising:
a delivery catheter with a tip that includes a tether clamp;
a retractable sheath;
a stent graft that includes a fabric tube attached to, and supported by, a self expanding stent, and a plurality of loops attached to at least one of the fabric tube and the self expanding stent, and each of the loops having, an opening, exposed on a radially outward side of the fabric tube;

a control tether;

the delivery system having a delivery configuration in which the stent graft is mounted on the delivery catheter in a compressed state and covered by the retractable sheath;

the delivery system being moveable from the delivery configuration to an adjustment configuration in which the retractable sheath is at a retracted position out of contact with the stent graft, and the control tether is held by the tether clamp, wrapped around the stent graft, and received through the openings of the loops;

the delivery system being moveable from the adjustment configuration to a release configuration in which the control tether is released from the tether clamp, wrapped around the stem graft, and received through the openings of the loops, and the stent graft is in an expanded state; and the delivery system being moveable from the release configuration to a detached configuration in which the stent graft is in the expanded state and the control tether is out of contact with the stent graft wherein the control tether is a monofilament wire;

wherein the tether clamp contacts the monofilament wire at three spaced apart locations around a circumference of the monofilament wire wherein the tether clamp includes a male part mated to a female part;

wherein one of the male part and the female part defines a V-shaped groove that includes two of three clamping surfaces that contact the monofilament wire at two of the three spaced apart locations; and an other one of the male part and the female part includes a clamping surface that contacts the monofilament wire at a remaining one of the three spaced apart locations.

16. A method of operating a controlled expansion stent graft delivery system that includes a delivery catheter with a tip that includes a tether clamp; a retractable sheath; a stent graft that includes a fabric tube attached to, and supported by, a self expanding stent that defines a longitudinal axis, and a plurality of loops attached to at least one of the fabric tube and the self expanding stent, and each of the loops having an opening exposed on a radially outward side of the fabric tube; and a control tether, and the method comprising the steps of:

positioning the delivery system at a treatment site in a delivery configuration in which the stent graft is mounted on the delivery catheter in a compressed state and covered by the retractable sheath;

changing the delivery system from the delivery configuration to an adjustment configuration in which the retractable sheath is at retracted position out of contact with the stent graft, and the control tether is held by the tether clamp, wrapped substantially completely around the longitudinal axis at the radially outward side of the fabric tube, and received through the openings of the loops;

changing the delivery system from the adjustment configuration to a release configuration in which the control tether is released from the tether clamp, wrapped around the longitudinal axis at the radially outward side of the fabric tube, and received through the openings of the loops, and the stent graft is in an expanded state; and changing the delivery system from the release configuration to a detached configuration in which the stent graft is in the expanded state and the control tether is out of contact with the stent graft.

17. The method of claim 16 including stopping expansion of the stent graft by increasing tension in the control tether while the delivery system is in the adjustment configuration;

adjusting at least one of an orientation and a position of the stent graft while the expansion of the stent graft is stopped; and resuming expansion of the stent graft by decreasing tension in the control tether.

18. The method of claim 17 wherein the stopping expansion step includes securing the control tether in a cleat.

19. The method of claim 16 including contracting the stent graft toward the compressed state by increasing tension in the control tether while the delivery system is in the adjustment configuration.

20. The method of claim 16 including moving the tether clamp to a release position responsive to increasing tension in a clamp release line.

* * * * *